United States Patent
Miraki

[19]

[11] Patent Number: 5,951,513
[45] Date of Patent: Sep. 14, 1999

[54] BALLOON CATHETER HAVING NON-BONDED INTEGRAL BALLOON AND METHODS FOR ITS MANUFACTURE

[75] Inventor: Manouchehr Miraki, Aliso Viejo, Calif.

[73] Assignee: Advanced Cardiovascular Systems, Inc., Santa Clara, Calif.

[21] Appl. No.: 08/873,071

[22] Filed: Jun. 11, 1997

Related U.S. Application Data

[63] Continuation of application No. 08/394,084, Feb. 24, 1995, abandoned.

[51] Int. Cl.⁶ .................................................. A61M 29/00
[52] U.S. Cl. ............................................. 604/96; 606/194
[58] Field of Search .............. 604/96, 101; 606/192–198

[56] References Cited

U.S. PATENT DOCUMENTS

| | | |
|---|---|---|
| 4,093,484 | 6/1978 | Harrison et al. . |
| 4,141,364 | 2/1979 | Schultze . |
| 4,178,937 | 12/1979 | Taylor et al. . |
| 4,210,478 | 7/1980 | Shoney . |
| 4,265,848 | 5/1981 | Rusch . |
| 4,490,421 | 12/1984 | Levy . |
| 4,624,657 | 11/1986 | Gould et al. . |
| 4,706,670 | 11/1987 | Andersen et al. ........................ 604/282 |
| 4,820,270 | 4/1989 | Hardcastle et al. . |
| 4,820,349 | 4/1989 | Saab . |
| 4,822,345 | 4/1989 | Danforth . |
| 4,935,190 | 6/1990 | Tennerstedt . |
| 4,976,689 | 12/1990 | Buchbinder et al. . |
| 5,087,394 | 2/1992 | Keith . |
| 5,102,416 | 4/1992 | Rock . |
| 5,152,772 | 10/1992 | Sewell, Jr. . |
| 5,171,221 | 12/1992 | Samson . |
| 5,195,962 | 3/1993 | Martin et al. . |
| 5,195,971 | 3/1993 | Sirhan ....................................... 604/96 |
| 5,223,205 | 6/1993 | Jackowski et al. . |
| 5,250,069 | 10/1993 | Nobuyoshi et al. . |
| 5,308,323 | 5/1994 | Sugawa et al. . |
| 5,378,230 | 1/1995 | Mahurkan . |
| 5,415,635 | 5/1995 | Bagaoisan et al. ........................ 604/96 |
| 5,496,275 | 3/1996 | Sirhan et al. ............................... 604/96 |
| 5,569,201 | 10/1996 | Burns . |
| 5,609,606 | 3/1997 | O'Boyle . |

FOREIGN PATENT DOCUMENTS

| | | |
|---|---|---|
| 0213748 | 3/1987 | European Pat. Off. . |
| 0213750 | 3/1987 | European Pat. Off. . |
| 0213749 | 4/1990 | European Pat. Off. . |
| 0569263 | 11/1993 | European Pat. Off. . |
| 3935579 | 5/1991 | Germany . |

*Primary Examiner*—Mark Bockelman
*Attorney, Agent, or Firm*—Heller Ehrman White & McAuliffe

[57] ABSTRACT

A method for manufacturing balloon catheters, and the catheters manufactured thereby. In accordance with the method, a workpiece comprising a tube-within-a-tube is placed within a mold, and a first region of the outer tube is distended into contact with the mold to form a seamless balloon of a desired configuration. The distension of the first region of the outer tube may be facilitated by electron beam irradiation, heating and/or longitudinal drawing of the workpiece concurrently with the introduction of a pressurized fluid into the space between the inner surface of the outer tube and the outer surface of the inner tube so as to exert the required outwardly distending pressure against the first region of the outer tube. When the method is utilized to form a "monorail" type of catheter, the inner tube need extend through only a distal portion of the outer tube, and the proximal end of the inner tube is coupled to an aperture formed in the sidewall of the outer tube to create a "monorail" type of a guide wire lumen. Alternatively, when used to form an over-the-wire type of catheter, the inner tube will extend through the entire length of the outer tube, and a proximal guidewire entry connector or port will be located on the proximal end of the catheter body to facilitate passage of the guidewire through the lumen of the inner tube.

6 Claims, 4 Drawing Sheets

BALLOON CATHETER HAVING NON-BONDED INTEGRAL BALLOON AND METHODS FOR ITS MANUFACTURE

This is a continuation of application Ser. No. 08/394,084 which was filed on Feb. 24, 1995, now abandoned.

FIELD OF THE INVENTION

The present invention pertains generally to medical equipment and more precisely to balloon catheters including, but not necessarily limited to, percutaneous transluminal balloon angioplasty catheters.

BACKGROUND OF THE INVENTION i. Typical Balloon Catheter and Procedures

Various types of balloon catheters are utilized in modern clinical medicine. Balloon catheters designed for transluminal angioplasty procedures usually incorporate a single dilation balloon formed on an outer surface of the catheter. The dilation balloon is sized and configured such that inflation of the balloon will effect dilation of an obstructive lesion within a blood vessel or other anatomical passageway. Balloon dilation angioplasty has become a widely accepted method of treating obstructions of the coronary and/or peripheral arteries.

A typical balloon angioplasty catheter comprises an elongate pliable catheter body having a proximal end, a distal end and at least one working lumen extending longitudinally through the catheter body to facilitate infusion of radiographic contrast media or other fluids. An inflatable dilation balloon is mounted on the outer surface of the catheter body, near the distal end thereof. A balloon inflation tube or lumen extends through the catheter body, from a balloon inflation port on the proximal end of the catheter, to the dilation balloon. The working lumen of the catheter may serve as a guide wire passage lumen, or a separate guide wire lumen may be provided apart from the working lumen through which fluids are infused. The guide wire lumen may extend through all, or a portion, of the catheter body to facilitate advancement of the balloon catheter over a prepositioned guide wire. Depending on whether the guide wire lumen extends through all or just a portion of the length of the catheter may be classified as a "monorail" catheter. Further descriptions of the typical "monorail" and "over-the-wire" catheter are as follows:

i. Monorail Catheters

In a "monorail" style catheter, a guide wire lumen extends through only a distal portion of the catheter, typically from a distal tip aperture to a proximal aperture formed in the side wall of the catheter body. Accordingly, as the catheter is advanced over the prepositioned guide wire, the proximal end of the guide wire will emerge from the side wall aperture such that the proximal portion of the guide wire remains outside of the catheter body as the catheter is advanced to its desired operative site. If it becomes necessary or desirable to exchange the balloon dilation catheter, the proximally exposed portion of the guide wire can be manually held and stabilized by the operator while the first catheter is removed and a second catheter is slid over the pre-positioned guide wire. Since the length of the catheter that must be passed over the guide wire is lessened in the "monorail" type of arrangement, it is typically easier for the operator to manually stabilize the guide wire during the exchange procedure and the need for a proximal extension or excessively long guide wire is eliminated.

ii. Over-the-Wire Catheters

The "over-the-wire" style of angioplasty catheter incorporates, a guide wire lumen which extends substantially through the entire length of the catheter. The guide wire lumen is separate from the balloon inflation lumen.

iii. Typical PTCA Procedure

In a typical percutaneous transluminal coronary angioplasty (PTCA) procedure a separate guiding catheter is initially inserted into a femoral artery or other peripheral artery. The guiding catheter is then advanced through the aorta to a position whereat the distal end of the guiding catheter is located adjacent or within the ostium of the coronary to be entered. Thereafter, an over-the-wire guide wire is inserted into the lumen of a balloon dilation catheter, and both wire and balloon catheter are advanced through the lumen of the guiding catheter. Thereafter, the guide wire is advanced into the obstructed coronary artery to a point where the distal end of the guide wire extends through the obstructive lesion. Thereafter, the balloon dilation catheter is advanced over the guide wire to a point where the dilation balloon is positioned within the obstructive lesion. Thereafter, the dilation balloon is inflated one or more times to dilate of the obstructive lesion, thereby relieving the obstruction of the coronary artery. After the lesion has been dilated, the dilation balloon is fully deflated and the balloon catheter, guiding catheter and guide wire are removed.

iv. Methods of Manufacturing Balloon Catheters

It is desirable that balloon dilation catheters, especially those of the type utilized for the above-described PTCA procedures, be constructed such that the dilation balloon is sufficiently strong to exert the required dilatory pressure against the offending lesion without causing rupture or disruption of the balloon. Also, because such balloon catheters are typically disposable items which are not intended to be reused, it is desirable that such catheters be manufactured as economically as possible to limit the expense associated with their clinical use.

The prior art has included methods for manufacturing balloon dilation catheters whereby the proximal and distal ends of the dilation balloon are affixed or bonded to the outer surface of a flexible cardiovascular catheter. However, such affixation or bonding of the balloon to the catheter typically results in the formation of seams or fusions which could fail or rupture during use.

There remains a need in the art for the development of new methods for manufacturing balloon catheters to eliminate the existence of catheter-balloon seams or fusions which could be subject to failure or leakage.

SUMMARY OF THE INVENTION

The present invention provides a method of manufacturing balloon catheters such that a balloon is formed as an integral portion of the catheter, without the need for fusing, bonding or affixing a separate balloon, or portion thereof, to the catheter body.

In accordance with the present invention there is provided a method for forming a balloon catheter. The basic method comprises the steps of:

a. providing an outer tube which has a proximal end, a distal end, a longitudinal axis, a hollow lumen extending longitudinally therethrough, an outer surface and an inner surface;

b. providing an inner tube which extends through at least a portion of the lumen of the outer tube, said inner tube having a proximal end, a distal end, a longitudinal axis, a hollow lumen extending longitudinally therethrough, an outer surface and an inner surface, the distal end of said inner tube being substantially co-terminus with the distal end of said outer tube;

c. causing the distal end of said outer tube to be sealed to the distal end of said inner tube;

d. causing a first region of said outer tube to become radially distended, to thereby form a balloon at said first region.

By the above-set-forth procedure, radial expansion of a specific region or segment of the outer tube serves to form the balloon on the outer surface of the catheter. The balloon formed by this method is integral of and continuous with the catheter body. There exists no seam, bond or fusion between the balloon and the catheter body. The open lumen of the inner tube may be used as a guide wire lumen or working lumen. The proximal end of the inner tube may be accessible at the proximal end of the catheter (i.e., an "over-the-wire" catheter) or may be accessible through an aperture formed in the side wall of the catheter body (i.e., a "monorail" catheter).

Further in accordance with the present invention, there are provided over-the-wire and monorail type balloon catheters manufactured by the above-set-forth method. Such catheters may include balloon dilation catheters of the type useable to perform balloon dilation angioplasty, or, any other type of balloon catheter used in clinical, industrial, research or other applications.

Further objects and advantages of the present invention will become apparent to those skilled in the art upon reading and understanding of the following detailed description, and consideration of the accompanying drawings.

DETAILED DESCRIPTION OF PREFERRED EMBODIMENTS

Figure 1:
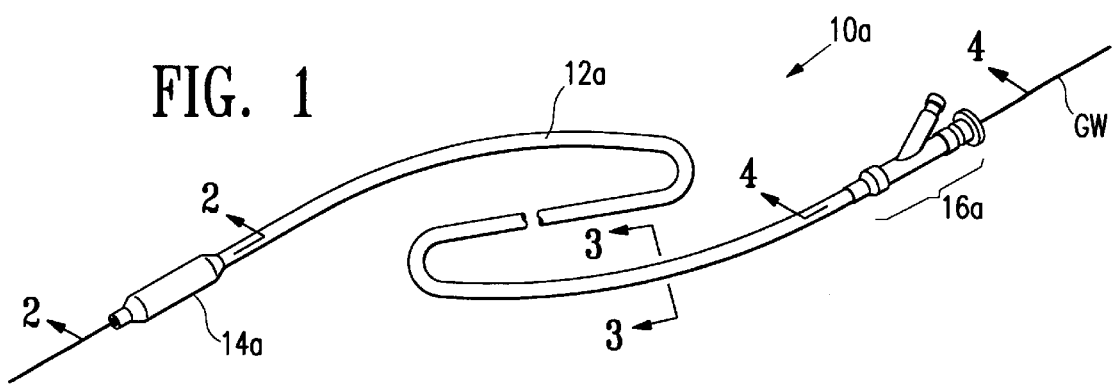
FIG. 1 is a perspective view of an over-the-wire balloon catheter manufactured in accordance with the present invention.
Figure 2:
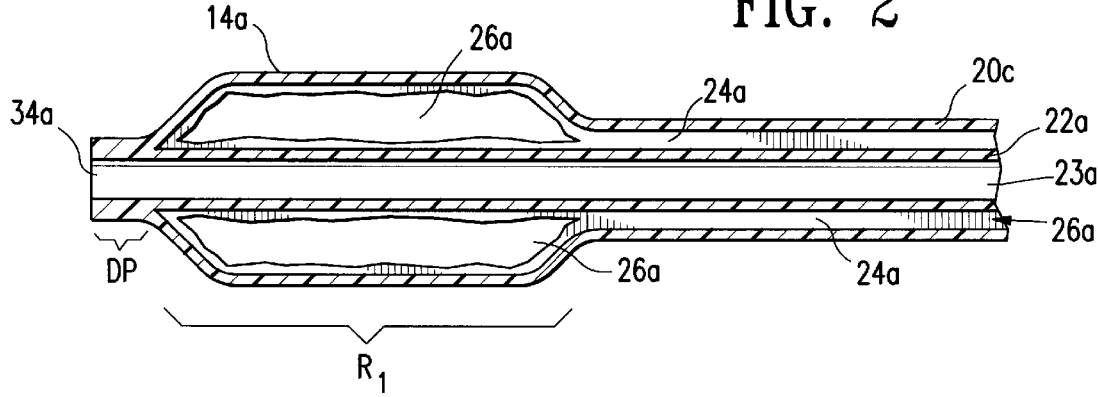
FIG. 2 is a longitudinal sectional view of the distal portion of the balloon catheter shown in FIG. 1.
Figure 3:
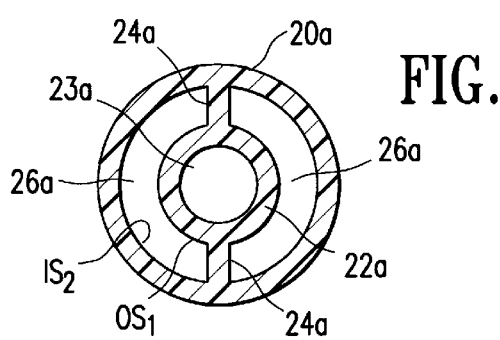
FIG. 3 is a cross-sectional view through line 3—3 of FIG. 1.
Figure 4:
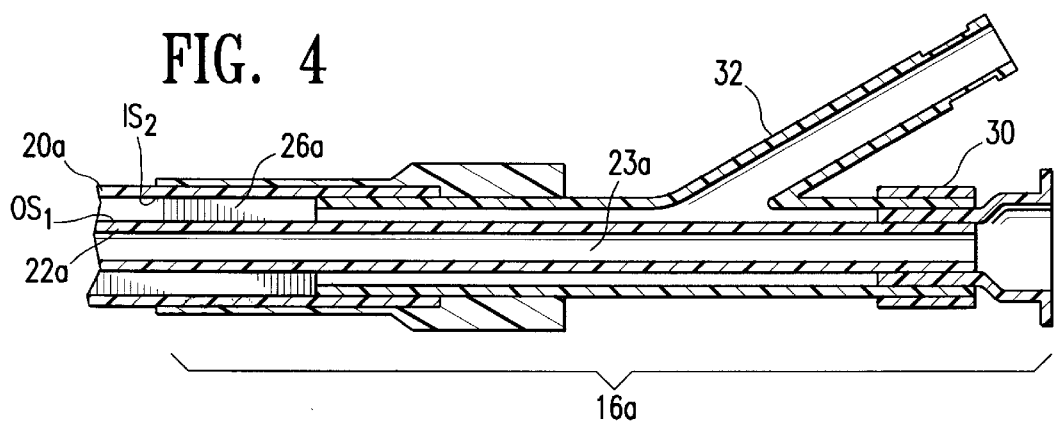
FIG. 4 is a longitudinal section view through line 4—4 of FIG. 1.
Figure 5:
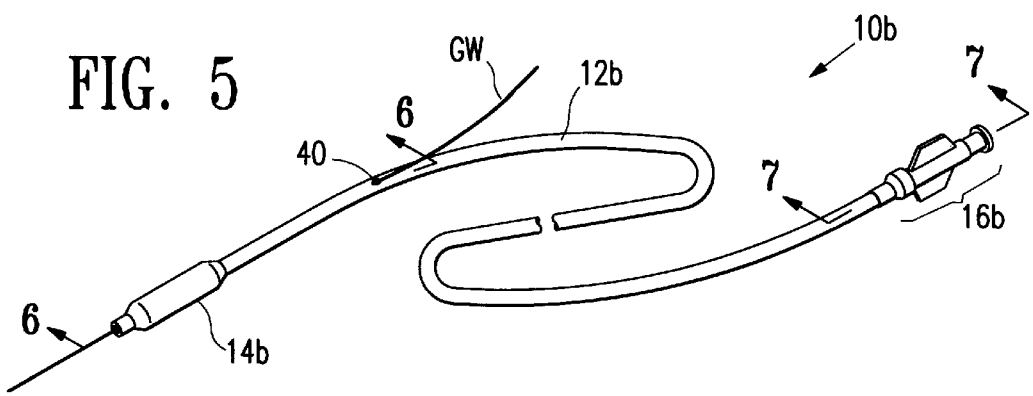
FIG. 5 is a perspective view of a monorail-type balloon catheter manufactured in accordance with the present invention.
Figure 6:
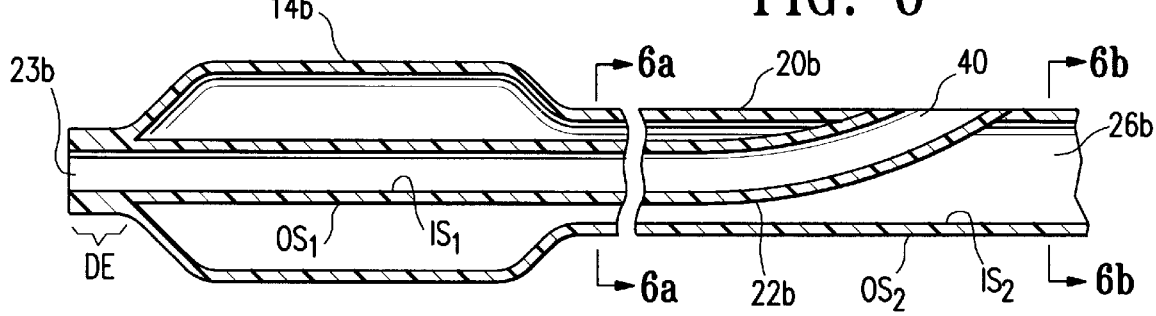
FIG. 6 is a longitudinal section view of the distal portion of the monorail catheter of FIG. 5.
Figure 6A:
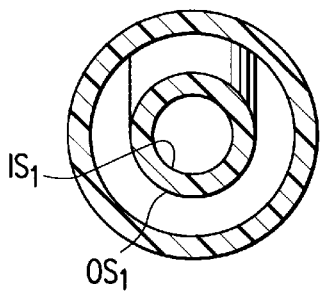
FIG. 6a is a cross sectional view through line 6a—6a of FIG. 6.
Figure 6B:
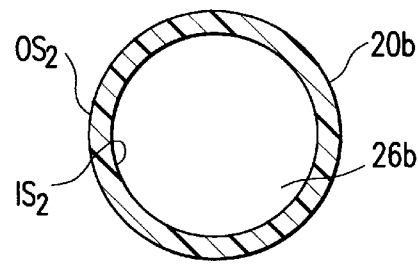
FIG. 6b is a longitudinal section view through line 6b—6b of FIG. 6.

The following detailed description and the accompanying drawings are provided for purposes of describing and illustrating presently preferred embodiments of the invention only and are not intended to limit the scope of the invention in any way.

FIGS. 1–4 shows an over-the-wire balloon catheter 10a formed in accordance with the present invention. As shown, the catheter 10a comprises an elongate pliable catheter body 12a having a balloon 14a formed near the distal end thereof, and a proximal Y connector 16a formed on the proximal end thereof.

The catheter body 12a is preferably formed of an extruded polyethylene tube-within-a-tube which comprises an outer tube 20a, an inner tube 22a and first and second connecting webs or frenula 24a. The webs or frenula 24a form connections between the outer surface $OS_1$ of the inner tube 22a and the inner surface $IS_2$ of the outer tube 20a. Such webs or frenula 24a are positioned on directly opposite sides of the inner tube 22a and are of equal length so as to hold the inner tube 22a in a coaxially centered position within outer tube 20a. Luminal space 26a exists between the inner surface $IS_2$ of the outer tube 20a and the outer surface $OS_1$ of the inner tube 22a, on either side of the webs 24a.

The distal ends of the inner tube 22a and outer tube 20a are substantially coterminous, as shown, and are welded, fused, bonded, adhered or otherwise sealed together to form a substantially solid distal portion DP of the catheter body 12a, thereby, preventing fluid from passing from the luminal space 26a out of the distal end of the catheter 10a.

A balloon 14a is formed near the distal end of the catheter 10a by radial distension of a region $R_1$ of the outer tube 20a, near the distal end thereof. Such radial distension of the region $R_1$ of the outer tube 20a may cause webs or frenula 24a to tear or separate within the region R, as shown. Or, such webs or frenula 24a may merely distend, but remain intact to act as inflation limiting webs which will help to deter over inflation and possible rupture of the balloon. As a result, there is created a substantially cylindrical balloon 14a which is formed integrally of with and continuous with the outer tube 20a, thereby avoiding any need to seal or bond the balloon to the catheter body 12a.

The proximal connector 16a positioned on the proximal end of the catheter 12a incorporates a first furcation or arm 30 and a second furcation or arm 32. The first furcation or arm 30 of the proximal connector 16a is coupled to and continuous with the lumen 23a of the inner tube 22a. By such arrangement, the proximal end of guide wire may be inserted into the distal end aperture 34a of the inner tube lumen 23a, and may be advanced through the entire length of the catheter 12a such that the proximal end of the guide wire will emerge out of the first furcation or arm 30 of the proximal connector 16a. Thus, because a guide wire may extend through substantially the entire length of the catheter 10a, such catheter 10a shown in FIGS. 1–4 is considered to be an over-the-wire type of catheter.

The second furcation or arm 32 of the proximal connector 16a is connected to and continuous with the luminal spaces 26a which exist between the outer surface $OS_1$ of the inner tube 22a and the inner surface $IS_2$ of the outer tube 20a. By such arrangement, balloon inflation fluid injected or withdrawn through second furcation or arm 32, will flow through luminal spaces 26a and into or out of the interior of the balloon 14a. Because the distal portion DP of the outer tube 20a is fused, bonded, adhered or otherwise sealed to the distal portion DP of the inner tube 22a, such balloon inflation fluid will be contained within the catheter 10a and will be prevented from leaking out of the distal end of the catheter body 12a.

An alternative "monorail" type of catheter is shown in FIGS. 5–8.

Figure 7:
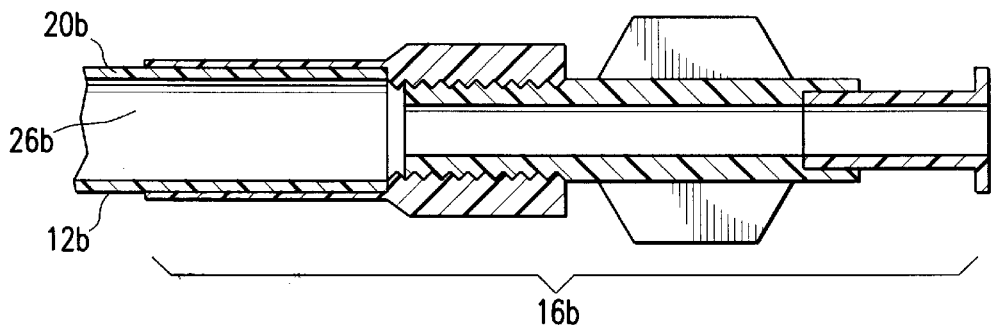
FIG. 7 is a longitudinal section view through line 7—7 of FIG. 5.

With reference to FIGS. 5–8, there is provided a monorail catheter 10b comprising an elongate pliable catheter body 12b having a balloon 14b formed near the distal end thereof and, as shown in FIG. 7 a proximal connector 16b mounted on the proximal end thereof.

The pliable catheter body 12b comprises an outer tube 20b having an inner surface $IS_2$ and an outer surface $OS_2$. A guide wire passage aperture 40 is formed in the sidewall of the outer tube 20b. The guide wire passage aperture may be any distance from DE, but in most adult PCTA catheters it is preferably about 40–150 mm from the distal end of the catheter body 12b. A second tube 22b extends longitudinally through a distal segment of the lumen 26b of the outer tube 20b. The proximal end of the inner tube 22b is fused, adhered or otherwise held in juxtaposition to the guide wire passage aperture 40 formed in the side wall of the outer tube 20b, as shown. The distal end of the inner tube 22b is substantially co-terminus with the distal end of the outer tube 20b. The distal portions DP of the inner tube 22b and outer tube 20b are fused, bonded, adhered or otherwise sealed together to prevent fluid from passing through lumen 26b out of the distal end of the catheter body 12b.

The inner tube 22b has an outer surface $OS_1$ and an inner surface $IS_1$. The inner surface $IS_1$ of the inner tube 22b defines a hollow lumen 23b which extends through the inner tube 22b and opens through the distal end of the catheter body 12b, as shown. By such arrangement, the proximal end of a guide wire GW may be inserted into the distal end opening of the lumen 23b of the inner tube 22b and advanced in the proximal direction such that the proximal end of the guide wire GW will emerge out of guide wire passage aperture 40, thereby allowing the catheter to pass through only a distal portion of the catheter body 12b. Thus, the configuration of the catheter 12b shown in FIGS. 5–8 is of the "monorail" catheter type.

A straight proximal connector 16b is positioned on the proximal end of the catheter body 12b. Such proximal connector 16b has a hollow inner bore which is coupled to and continuous with the lumen 26b of the outer tube 20b. By such arrangement, balloon inflation fluid which is infused into, or withdrawn from, proximal connector 16b will flow through the outer tube lumen 26b, around the outer surface $OS_1$ of the inner tube 22b and into or out of the interior of the balloon 14b.

The balloon 14b comprises a radially distended region R1 of the outer tube 20b. Such radially distended region R1 of the outer tube 20b is, in the embodiment shown, of substantially cylindrical configuration. Such cylindrical configuration is achieved, as described herebelow, by the positioning of a cylindrical balloon form member about the first region of the outer tube prior to radial distension thereof. It will be appreciated that many other configurations of the balloon may also be achieved by using different configurations of a form member positioned about the first region of the outer tube such that, when the first region of the outer tube undergoes radial distension, it will come into contact with the surrounding balloon form member, thereby causing the balloon to assume the form or configuration of the surrounding form member or mold.

A Preferred Manufacturing Method

Figure 8A:
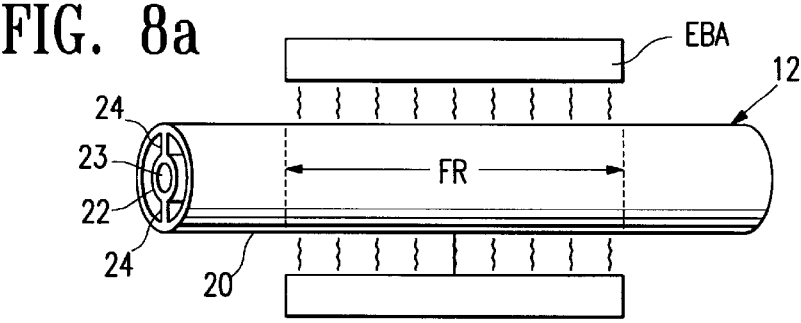
FIGS. 8a–8d are step-wise schematic showings of a preferred balloon catheter manufacturing method in accordance with the present invention.
Figure 8B:
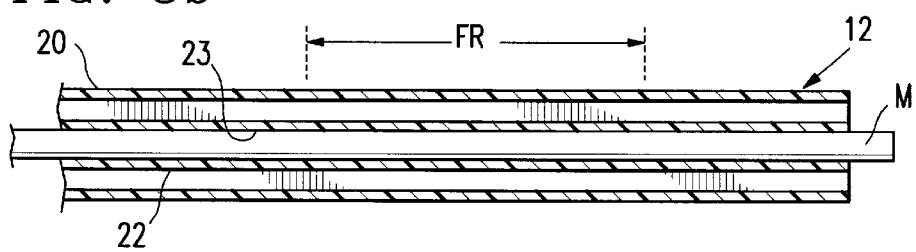

In accordance with the present invention, a preferred method for manufacturing the balloon catheter 10 is shown in FIGS. 8a–8b. In particular, FIGS. 8a–8b depict the formation of an over the wire balloon catheter 10a using a tube-within-a-tube type of construction as shown in FIGS. 1–4 hereof. It will be appreciated, however, that the manufacturing method described herebelow may also be utilized to form a "monorail" type catheter of the type shown in FIGS. 5–8 hereof.

FIGS. 8a–g show a step-by-step method of manufacturing the catheter body 12 of a balloon catheter of the present invention.

As shown in FIG. 8a, the initial workpiece is the rudimentary catheter body 12. This workpiece 12 is preferably formed of extrudeable polyethylene material, and comprises an inner tube 22 disposed within an outer tube 20. Connection members, such as webs or frenula 24 extend between the outer surface of the inner tube 22 and the inner surface of the outer tube 20 so as to hold the inner tube 22 in a coaxially centered position within the lumen 26 of the outer tube.

As shown in FIG. 8a, an electron beam irradiation apparatus EBA is utilized to pass electron beam radiation onto the first region FR of the outer tube 20. This first region FR is the portion of the outer tube 20 which is to be subsequently formed into the catheter balloon. Such irradiation results in softening of the first region FR of the outer tube 20 which is to subsequently be formed into the balloon.

Thereafter, as shown in FIG. 8b, a rigid mandrel M, such as a stainless steel rod, is inserted into the lumen 23 of the inner tube 22 to maintain the original size and configuration of the inner tube 22 during the subsequent procedure.

Figure 8C:
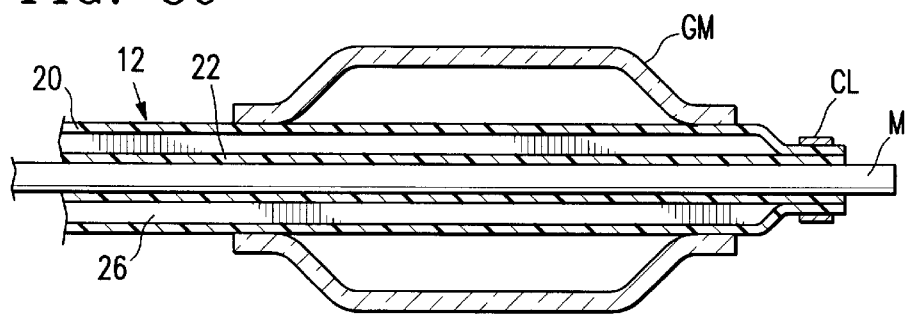

Thereafter, as shown in FIG. 8c, the distal portion of the catheter body 12 is inserted into a suitable mold, preferably a glass mold GM having an internal configuration which is analogous to the intended configuration of the balloon to be formed. An annular clamp CL is applied to distal end of the catheter body 12 to exert radially inward pressure or compression of the inner surface of the outer tube 20 against the outer surface of the inner tube 22, and the inner surface of the inner tube 22 against the rigid mandrel M which is inserted therein. In this regard, the clamp CL is applied in a manner which forms a gas tight seal of the lumenal space 26 of the outer tube 20, at the distal end of the catheter body. This prevents leakage of gas from the lumenal space 26 during the subsequent steps of the manufacturing process.

Figure 8D:
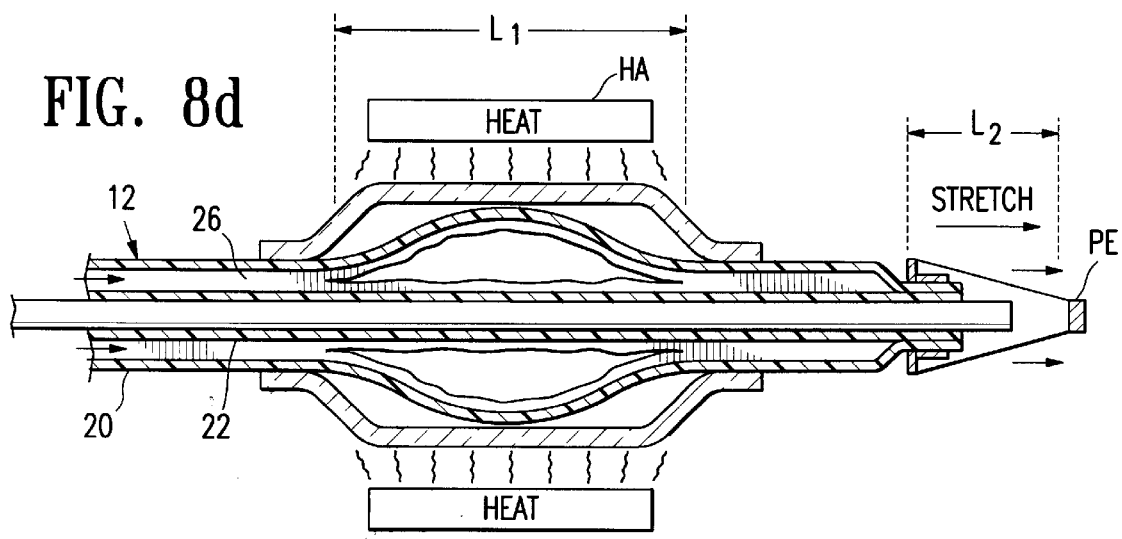

Thereafter, as shown in FIG. 8d, a heating apparatus HA is utilized to apply heat through the glass mold GM, so as to warm the first region FR of the workpiece 12 positioned within the glass mold GM. Concurrently with the application of heat from the heating apparatus HA, a pressure source (not shown) is utilized to pass positive pressure fluid (e.g., compressed air) into the lumenal space 26 between the outer surface of the inner tube 22 and the inner surface of the outer tube 20. Such positive pressure fluid causes the softened and heated first region FR of the outer tube 20 to undergo outward radial expansion within the surrounding glass mold, as shown. Also concurrently therewith, a pulling element PE is used to draw or pull the distal end of the workpiece 12 in the distal direction, thereby lengthening the heated first region FR of the workpiece which resides within the glass mold GM and causing the heated first region FR of the outer tube 20 and inner tube 22 to become extruded, and decreased in thickness. In the preferred method, the increase $L_2$ in length of the workpiece 12 preferably equals to approximately one half (½) of the length $L_1$ of the first region FR of the workpiece 12.

Figure 8E:
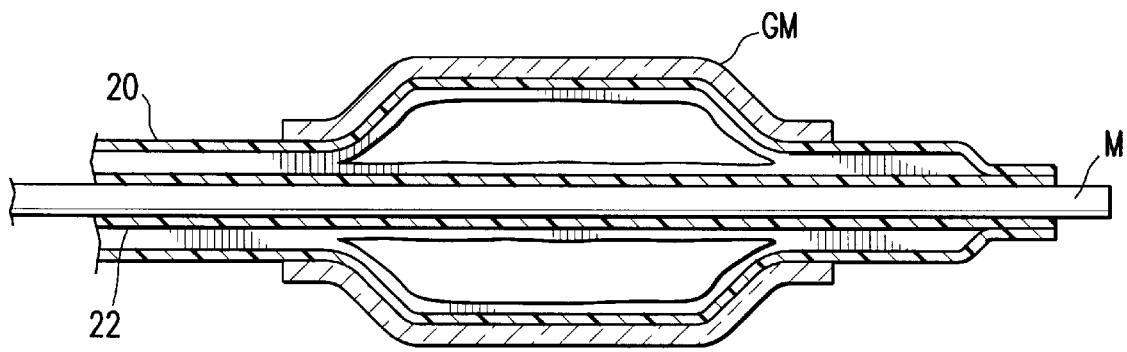

As shown in FIG. 8e, after the concurrent radial distension and longitudinal drawing have been completed, the first region FR of the outer tube 20 will have distended and conformed to the shape of the surrounding inner surface of the glass mold GM. At this time, the heating apparatus HA is removed or turned off and the catheter body 12 is permitted to cool. The clamp CL is removed from the distal end of the catheter body 12, and the positive pressure is released from the lumenal space 26 thereby allowing the newly created balloon 14 to become deflated.

Figure 8F:
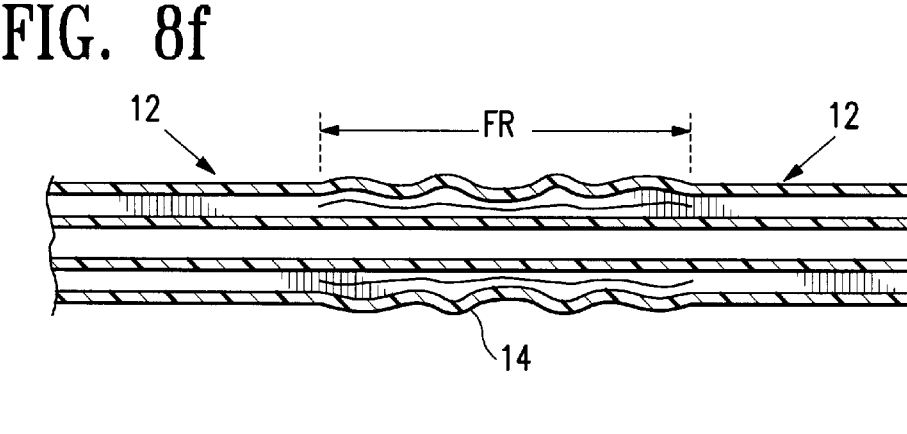

As shown in FIG. 8f, the workpiece 12 is removed from the glass mold GM and the rigid mandrel M is removed. A cutting apparatus is utilized to cut the distal end of the workpiece 12, thereby removing the portion of the distal end which had previously been compressed within the clamp CL.

Figure 8G:
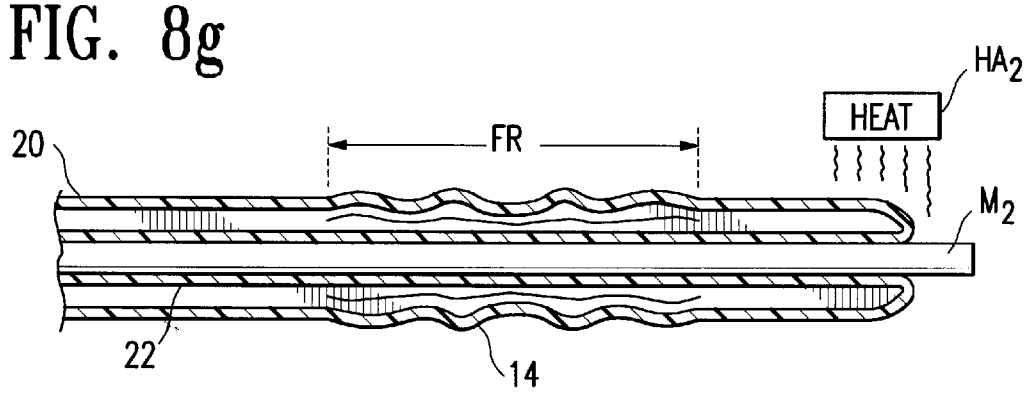

Thereafter, as shown in FIG. 8g, a second rigid mandrel M₂ is inserted into the distal end of the lumen 23 of the inner tube 22, and a second heating apparatus HA₂ is utilized to heat-fuse or thermally weld the distal end of the outer tube 20 to the distal end of the inner tube 22, thereby completing the transformation of the original workpiece into a catheter body 12 having a smooth distal tip through which the inner tube lumen 23 opens.

Thus, the steps of the method shown in FIGS. 8a–8g result in the formation of a balloon catheter body 12 of an over-the-wire catheter of the type shown in FIGS. 1–4 of this patent application.

It will be appreciated that the invention has been described herein with reference in terms of presently preferred or exemplary embodiments only. No effort has been made to exhaustively describe each and every embodiment in which the device of the present invention may take physical form, or by which the method of the present invention may be practiced. Indeed, it will be appreciated by those skilled in the art, that various modifications, additions, deletions and changes may be made to the herein-described preferred embodiments without departing from the intended spirit and scope of the present invention.

What is claimed is:

1. A balloon catheter which is manufactured by the steps of:
   a) forming an elongated shaft having an outer tubular member, an inner tubular member having a guidewire receiving inner lumen extending therein and being disposed within the outer tubular member and defining an inflation lumen therebetween, and at least one web within the inflation lumen interconnecting the inner and outer tubular members;
   b) sealing together distal extremities of the inner and outer tubular members;
   c) softening a distal portion of the outer tubular member;
   d) subjecting an interior of the softened distal portion to internal fluid pressure to expand the softened distal portion to a larger diameter than other portions of the outer tubular member and to separate at least a portion of the web extending within the softened distal portion, to form a balloon having a continuous interior in fluid communication with the inflation lumen; and
   e) securing an adapter on a proximal extremity of the elongated shaft having a first arm which has a proximal end, a port in the proximal end, and a first inner lumen in fluid communication with the inflation lumen and the port in the proximal end of the first arm, and a second arm with a second lumen in communication with the guidewire lumen.

2. The balloon catheter of claim 1 including a sealing fusion bond between the distal extremities of the inner and outer tubular members.

3. A balloon dilatation catheter comprising:
   a) an elongated shaft having proximal and distal sections, a distal end, a port in the distal end, an outer tubular member, an inner tubular member having a guidewire receiving inner lumen extending to the port in the distal end and being disposed within the outer tubular member and defining an inflation lumen between the inner and outer tubular members, and at least one elongated web extending between the inner tubular member and the outer tubular member within the inflation lumen in the distal shaft section;
   b) a dilatation balloon on the distal section of the elongated shaft having a continuous interior in fluid communication with the passageway between the inner and outer tubular members, the at least one web extending within the interior of the balloon; and
   c) an adapter on a proximal extremity of the elongated shaft having a first arm which has a proximal end, a port in the proximal end, and a first inner lumen in fluid communication with the port in the proximal end of the first arm and the inflation lumen between the inner and outer tubular members, and a second arm with a second inner lumen in fluid communication with the guidewire receiving inner lumen in the inner tubular member.

4. The balloon dilatation catheter of claim 3 wherein the dilation balloon is formed from part of the outer tubular member.

5. The balloon dilatation catheter of claim 3 including a pair of webs extending between and interconnecting the inner and outer tubular members.

6. A balloon dilatation catheter comprising:
   a) an elongated shaft having proximal and distal sections, a distal end, a port in the distal end, an outer tubular member, an inner tubular member having a guidewire receiving inner lumen extending to the port in the distal end and being disposed within the outer tubular member and defining an inflation lumen between the inner and outer tubular members, and at least one elongated web extending between the inner tubular member and the outer tubular member within the inflation lumen in the distal shaft section; and
   b) a dilatation balloon on the distal section of the elongated shaft having a continuous interior in fluid communication with the passageway between the inner and outer tubular members, the at least one web extending within the interior of the balloon and having a separate portion.

* * * * *